United States Patent
Hodges et al.

[11] Patent Number: 5,916,172
[45] Date of Patent: Jun. 29, 1999

[54] DIAGNOSIS OF NEUROMUSCULAR DYSFUNCTION

[75] Inventors: Paul William Hodges, Taringa; Carolyn Anne Richardson, St. Lucia, both of Australia

[73] Assignee: The University of Queensland, Queensland, Australia

[21] Appl. No.: 08/930,376

[22] PCT Filed: Mar. 29, 1996

[86] PCT No.: PCT/AU96/00183
§ 371 Date: Dec. 30, 1997
§ 102(e) Date: Dec. 30, 1997

[87] PCT Pub. No.: WO96/29929
PCT Pub. Date: Oct. 3, 1996

[30] Foreign Application Priority Data

Mar. 29, 1995 [AU] Australia ............................... PN 2050

[51] Int. Cl.$^6$ ........................................... A61B 5/04
[52] U.S. Cl. ........................................... 600/546; 600/595
[58] Field of Search .................................... 600/546, 587, 600/594, 595

[56] References Cited

U.S. PATENT DOCUMENTS

| | | |
|---|---|---|
| 4,163,440 | 8/1979 | DeLuca et al. |
| 5,085,225 | 2/1992 | DeLuca et al. |

FOREIGN PATENT DOCUMENTS

| | | |
|---|---|---|
| 1 220 272 | 4/1987 | Canada. |
| 0 336 030 A1 | 10/1989 | European Pat. Off. |
| WO 94/07414 | 4/1994 | WIPO. |

OTHER PUBLICATIONS

DiFabio, R.P. 1987, Physical Therapy 67:43–48.
Troyer, A.D. et al., 1990, J. App. Physiol. 68:1010–1016.
Bouisset, S. et al., 1987, J. Biomechanics 20:735–742.
Panjabi, M.M., 1992, J. Spinal Disorders 5:383–389.
Panjabi, M.M., 1992, J. Spinal Disorders 4:390–397.
Cresswell, A.G., et al., 1994, Exp. Brain 98:336–341.
Cresswell, A.G., et al., 1992, Acta Physiol. Scand 144:409–418.
Soderberg, G.L. et al., 1983, Spine 8:79–85.
Belen'KII, V. Ye., et al., 1967, Biofizika 12:135–141.
Oddsson, L., 1989, Acta Physiol Scand 136:47–58.

(List continued on next page.)

*Primary Examiner*—Cary O'Connor
*Assistant Examiner*—Pamela L. Wingood
*Attorney, Agent, or Firm*—Stroock & Stroock & Lavan LLP

[57] ABSTRACT

A diagnostic apparatus for diagnosis of lower back pain (LBP) caused by neuromuscular dysfunction, said diagnostic apparatus comprising:

a monitoring means for monitoring an anticipatory muscle signal resulting from one or more electrodes associated with an anticipatory muscle and a prime mover muscle signal resulting from one or more electrodes associated with at least one prime mover muscle associated with a limb; and a processing means for detecting a variation in the time of onset of the anticipatory muscle signal relative to the time of onset of the prime mover muscle signal for providing diagnosis of presence or absence of LBP.

There is also provided a method for diagnosis of LBP caused by neuromuscular dysfunction said method including the steps of:

(i) initiating a voluntary movement of a limb;
(ii) electrically monitoring activation of at least one anticipatory muscle relative to activation of at least one prime mover muscle associated with the limb, and
(iii) comparing time of onset of activation of the at least one anticipatory muscle relative to time of onset of activation of the at least one prime mover muscle to diagnose presence or absence of LBP.

38 Claims, 5 Drawing Sheets

OTHER PUBLICATIONS

Basmajian, J.V. et al., 1962, 849.
Mayer, T.G., et al. 1989, Spine.
Hides, J.A., et al. 1994, Spine 19:165–172.
Goel, V.K. et al. 1993, Spine 18:1531–1541.
Panjabi, M., et al. 1989, Spine 14:194–199.
Johansson, H., et al., 1991, Med. Hypoth. 35:196–203.
Hides, J.A., et al., 1995, Spine 20: 54–58.
Gollhofer, A., et al., 1991, Int. J. Sports Med. 12: 34–40.
Johansson, H., et al., 1991, Biomed. Eng 18:341–368.
Baratta, R., et al., 1988, Am J. Sports Med. 16:113–122.
Hoffer, J.A., et al., 1981, J. Neurophysiol. 45: 282–285.

DIAGNOSIS OF NEUROMUSCULAR DYSFUNCTION

FIELD OF THE INVENTION

THIS INVENTION relates to diagnosis of neuromuscular dysfunction and, in particular, a system and a method for diagnosis of low back pain caused by neuromuscular dysfunction.

BACKGROUND ART

Low back pain (LBP) produces major societal, industrial, and personal problems, resulting in substantial annual health care costs, lost productivity, and disability (Flicker et al., 1993, Spine, 18, 582–586). Only a small percentage of low back complaints can be diagnosed definitively (Nachemson, 1975, NINCDS, Monograph No. 15, US Department of Health, Education and Welfare) because current techniques are effective only for diagnosis of LBP associated with damage or abnormality of the skeleton. However, a substantial percentage of these complaints can not be diagnosed because existing techniques are ineffective for diagnosis of LBP associated with muscular dysfunction.

The importance of the muscular system in stabilising the lumbar spine is summarised in an article by Goel et al., (1993, Spine, 18, 1531–1541). The paraspinal muscles, in particular, have been shown to play a vital role in the stability and functional movement of the vertebral column but their role in spinal dysfunction is unclear. In this respect, reference may be made to studies in which it was determined that the lumbar multifidus (Kalimo et al., 1989, Ann. Med., 21, 353–359; Punjabi et al., 1989, Spine, 14, 194–200; Wilke et al., 1995, Spine, 20, 192–198) and the lumbar erector spinae (McGill, 1991, Spine, 16, 809–815; Soderberg and Barr, 1993, Spine, 8, 79–85; Sullivan, 1989, Phys. Ther., 69, 38–45) are important in stabilisation of the lumbar spine.

Instability of the lumbar motion segment which often manifests in the neutral zone motion, is implicated as an important factor in the development of recurrent and chronic LBP (Punjabi, 1992, J. Spinal Disord., 5, 383–389; Panjabi, 1992, J. Spinal Disord., 5, 390–397). In an article by Hides et al. (1994, Spine, 19, 165–172) reference is made to unilateral wasting of paraspinal muscles localised to one vertebral level in patients with acute/subacute LBP. Paraspinal muscle wasting also has been documented in post-operative patients (Laasonen, 1984, Neuroradiology, 26, 9–13; Mayer et al., 1989, Spine, 14, 33–36; Sihvonen et al., 1993, Spine, 18, 575–581) and in subjects with chronic LBP (Cooper et al., 1992, Br. J. Rheumatol., 31, 389–394; Tertti et al., 1991, Radiology, 180, 503–507).

The muscle system, through specific joint stabilisation strategies, can help minimise joint displacement, aid stress absorption and generally prolong the "cartilage serving time" of the joint (Baratta et al., 1988, Am. J. Sp. Med., 16, 113–122). Several muscle recruitment strategies have been implicated in the development of active joint stabilisation. In this respect, reference may be made to articles by Gollhofer and Kyrolainen (1991, J. Sp. Med., 12, 3440), Johansson et al., (1991, CRC Crit., Rev. Biom. Eng., 18, 341–368), Woo and Winters (1990, Multiple Muscle Systems, New York, Springer-Verlag), Hoffer and Andreassen (1981, J. Neurophysiol., 45, 267–285) and Johansson and Sojka (1991, Med. Hypotheses, 35, 196–203).

One strategy which is described in conjunction with joint stabilisation, is the early pre-programmed recruitment of particular muscles. These muscles are activated in anticipation of a prime mover of voluntary limb or trunk movement in normal individuals and are hereinafter referred to as anticipatory muscles. Pre-programmed muscle recruitment serves to ensure that the joint is supported prior to movement. For example, during a jumping task, the leg extensor muscles are recruited prior to ground contact (Gollhofer and Kyrolainen, 1991, J. Sp. Med., 12, 34–40).

In addition, activation of postural muscles has been shown to occur in anticipation of the prime mover of voluntary limb or trunk movement to prevent the inevitable disturbance to balance. In this respect, reference may be made to Belen'kii et al., (1967, Biofizika, 12, 135–141), Bouisset and Zattara (1987, J. Biomech., 20, 735–742) and Oddsson (1989, Acta Physiol. Scand., 136, 47–58).

Reference also may be made to studies by Cresswell et al., (1992, Acta Physiol. Scand., 144, 409–418; Cresswell et al., 1994, Exp. Brain Res., 98, 336–341) in which it was shown that the transversus abdominis (TA) is activated with all trunk movements regardless of the primary direction of movement and is recruited prior to all other abdominal muscles with sudden perturbations of the trunk. The preactivation of TA with self loading was considered to be a component of a feed-forward postural strategy to increase the stability of the trunk by increasing the stiffness of the intervertebral joints of the lumbar spine (Cresswell et al., 1994, Exp. Brain Res., 98, 336–341).

The aforementioned references highlight the importance of the muscular system, and in particular, the paraspinal muscles, in the segmental stabilisation of the lumbar spine and in preparation of the disturbance to balance. However, at present, it is not possible to measure directly the strength of individual paraspinal muscles in order to diagnose muscular dysfunction associated with LBP. As a consequence, imaging techniques have been used to measure muscle size, and the relative advantages of ultrasound imaging, computed tomography (CT) scanning, and magnetic resonance imaging (MRI) in rehabilitation have been presented (Stokes and Young, 1986, Physioth. Prac., 2, 31–36).

In an article by Hides et al., (1995, Spine, 20, 54–58) reference is made to a comparison of real-time (RT) ultrasonography and MRI in respect of measurement of lumbar multifidus cross-sectional area. In this study, it was reported that, in contrast to MRI, RT ultrasonography was less expensive and more widely accessible. However, it was also stated that excluding the measurement of large muscles, RT ultrasonography had the disadvantage of a relatively limited field of view and was unable to provide pilot sections for confirmation of vertebral levels when imaging the spine. As a consequence of these limitations, the authors suggested that strict protocols should be followed to allow accurate measurement of the soft tissues.

In a prior article by Hides et al., (1994, Spine, 19, 165–172), the effect of LBP on the size of the lumbar multifidus was examined using RT ultrasonography. This study showed that the localisation of multifidus wasting is likely to be due to inhibition of perceived pain via a long-loop reflex pathway. However, there was a lack of correlation between severity of paraspinal muscle wasting and symptoms. This lack of correlation highlighted the requirement for objective measurement of paraspinal muscular dysfunction in LBP.

Most techniques available currently to assess muscular dysfunction are either non-objective or they lack clinical validation and reliability. One technique that does provide objective data uses electromyographic (EMG) spectral analysis of lower back muscles. Although some prior EMG systems provided advantages over other techniques, these suffered certain deficiencies resulting primarily from treatment of individual muscle groups as a continuous muscle mass and exclusive reliance on the amplitude of EMG signals. In this respect, reference may be made to Gilmore and DeLuca (1985, IEEE Trans. Biomed. Eng BME, 32, 75–78); Roy et al., (Computer Aided Back Analysis System, IEEE Engineering in Medicine and Biology Society - 10th Annual International).

In U.S. Pat. No. 4,655,227 reference is made to a method and equipment based on analysis of EMG activities for the detection of mechanical injuries in the lumbar spine of a patient and the identification of the injuries, using a mathematical model applicable to the five lumbar vertebrae of a human being, and to their disc. This specification, however, did not disclose a method or an apparatus for diagnosis of muscular dysfunction.

Reference may also be made to U.S. Pat. No. 5,086,799 and 5,163,440 which respectively describe a system and a method for the detection of muscular dysfunction based on analysis of EMG activities in association with muscular fatigue.

Electromyographic studies have also been used in association with high resolution ultrasound to record the behaviour of the TA muscle relative to the external oblique (EO) and rectus abdominis (RA) in humans (Troyer et al., 1990, J. Appl. Physiol. 68, 1010–1016). These studies showed that TA is recruited preferentially to the superficial muscle layer of the abdominal wall (RA and EO) during breathing. However, these studies did not provide a correlation between the measurement of activation of TA and LBP.

Reference also may be made to an article by Di Fabio (1987, Phys. Ther., 67, 43–48) in which an EMG was used in concert with a computer analysis system (CAS) for the determination of the temporal sequence of muscle contraction. This study showed that when CAS was used for the detection of EMG muscle burst onset, it demonstrated perfect reliability and was superior to visual inspection of the data. However, this study was limited to the measurement of the temporal sequence of activation of four lower extremity muscles in response to unexpected balance perturbations and was not used for the analysis of lumbar muscular dysfunction associated with LBP.

From the foregoing, it is evident that certain techniques exist that are less than satisfactory for the effective diagnosis of LBP caused by neuromuscular dysfunction.

OBJECT OF THE INVENTION

It is an object of the invention to provide an apparatus and a method for diagnosis of LBP caused by neuromuscular dysfunction.

SUMMARY OF THE INVENTION

According to one aspect of the invention, there is provided a diagnostic apparatus for diagnosis of LBP caused by neuromuscular dysfunction, said apparatus comprising:

a monitoring means for monitoring an anticipatory muscle signal resulting from one or more electrodes associated with an anticipatory muscle and a prime mover muscle signal resulting from one or more electrodes associated with at least one prime mover muscle associated with a limb; and a processing means for detecting a variation in the time of onset of the anticipatory muscle signal relative to the time of onset of the prime mover muscle signal for providing diagnosis of presence or absence of LBP.

Suitably, the apparatus is adapted to diagnose LBP when activation of the prime mover muscle occurs before activation of the anticipatory muscle or alternatively when activation of the prime mover muscle and the anticipatory muscle occurs simultaneously. The apparatus is further adapted to diagnose absence of LBP when activation of the anticipatory muscle occurs before activation of the prime mover muscle.

Preferably, the apparatus further comprises a signal generator means for generating one or more instruction signals.

Suitably, the signal generator means is adapted to generate two sequential instructions.

Preferably, the signal generator means is adapted to provide a time delay.

Suitably, the time delay is random.

Preferably, the processing means being provides an output signal indicative of the presence or absence of LBP wherein the output signal is provided when the prime mover muscle signal and anticipatory muscle signal increase above a threshold value. Suitably, there is a different threshold value associated with each of the prime mover muscle signal and anticipatory muscle signal wherein the respective threshold values are manually adjustable.

Preferably, the processing means is adapted to calculate each of the threshold values.

Suitably, the apparatus further comprises a signal conversion means to convert both the prime mover muscle signal and anticipatory muscle signal into corresponding digitised signals.

The apparatus may also include a digital storage means for storing the digitised signals.

Preferably, the processing means is a computer or programmable processor.

Suitably, the digital storage means is part of a computer, or programmable processor, wherein the computer is programmed to analyse the digitised signals.

Preferably, the apparatus is adapted to average the digitised signals over a period of time to provide signal reference values.

Suitably, the programmable processor or computer is programmed to process the digital signals wherein the digitised signals are averaged over a period of time to provide signal reference values.

Preferably, the processing means provides an output signal indicative of the presence or absence of LBP when the prime mover muscle signal increase above the corresponding signal reference values thereof.

According to another aspect of the invention, there is provided a method for diagnosis of LBP caused by neuromuscular dysfunction, said method including the steps of:

(i) initiating a voluntary movement of a limb;
(ii) electrically monitoring activation of at least one anticipatory muscle relative to activation of at least one prime mover muscle associated with the limb; and
(iii) comparing time of onset of activation of the at least one anticipatory muscle relative to time of onset of activation of the at least one prime mover muscle to diagnose presence or absence of LBP.

Suitably, presence of LBP is diagnosed when the time of onset of activation of the prime mover muscle occurs before the time of onset of activation of the anticipatory muscle. On the other hand, absence of LBP maybe diagnosed when the time of onset of activation of the anticipatory muscle occurs prior to or concurrent with the time of onset of activation of the prime mover muscle.

Preferably, the method further includes the step of generating one or more instruction signals to instruct voluntary movement of the limb.

Suitably, there are two instruction signals which are sequential wherein a first instruction signal functions as a warning signal which informs the patient to prepare for voluntary movement of the limb associated with the prime mover muscle and a second instruction signal instructs voluntary movement of the limb.

Preferably, there is a time frame between each of the instruction signals.

In preference, the time frame is random.

Preferably, the method further includes the step of determining when an electrical signal associated with activation of the prime mover muscle and an electrical signal associated with activation of the anticipatory muscle increase above a threshold value.

Suitably, there is a different threshold value associated with the activation of each of the electrical signals.

The method may further include the step of analysing multiple measurements to validate the diagnosis.

In preference, the method further includes the step of determining a muscle signal reference value associated with respective anticipatory and prime mover muscles when relaxed by averaging signals from respective muscles over multiple measurements.

In such a case, the one or more instruction signals for effecting voluntary movement of the limb result in an increased magnitude value of each of the electrical signals associated respectively with activation of the anticipatory muscle and the prime mover muscle.

Suitably, the method further includes the step of averaging the electrical signals over a period of time to provide an average magnitude value.

Preferably, the method further includes the step pf comparing each of the electrical signals associated respectively with activation of the anticipatory muscle and the prime mover muscle when the average magnitude value of each of the signals increases above a respective threshold value to provide a time sequence. In such a case, the threshold value of the anticipatory muscle signal is related to an anticipatory muscle signal reference value and the threshold value of the prime mover muscle signal value is related to a prime mover muscle signal reference value.

Diagnosis of the presence of LBP occurs when the average magnitude value of the prime mover muscle signal increases above the threshold value thereof, prior to when the average magnitude value of the anticipatory muscle signal increases above the threshold value thereof.

Alternatively, absence of LBP is diagnosed when the average magnitude value of the anticipatory muscle signal increases above the threshold value thereof, prior to or concurrent with when the average magnitude value of the prime mover muscle signal increases above the threshold value thereof.

Suitably, processing of each of the signals results in conversion of the electrical signals into digitised signals; and
storing the digitised signals for subsequent use.

Examples of anticipatory muscles discussed above include the transverses abdominis and multifidus. Examples of prime mover muscles referred to above are the anterior deltoid, middle deltoid and posterior deltoid.

Each of the abovementioned anticipatory muscles and prime mover muscles are associated with the upper limbs of the arms of a patient who may be suffering from LBP. The initial voluntary movement of a limb may refer to flexion, abduction or extension of the limb.

It will also be appreciated that the method of the invention may be applied to the lower limbs or legs of the patient. In this specific embodiment, examples of anticipatory muscles are transversus abdominis, internal oblique, external oblique, rectus abdominis and multifidus and examples of the prime mover muscles are rectus femoris, tensor fascialatae, biceps femoris, gluteus maximus, semi-membranosis and semi-tendonosis.

In order that the invention may be readily understood and put into practical effect, reference will now be made to a preferred embodiment and flow diagrams in which.

Figure 1:
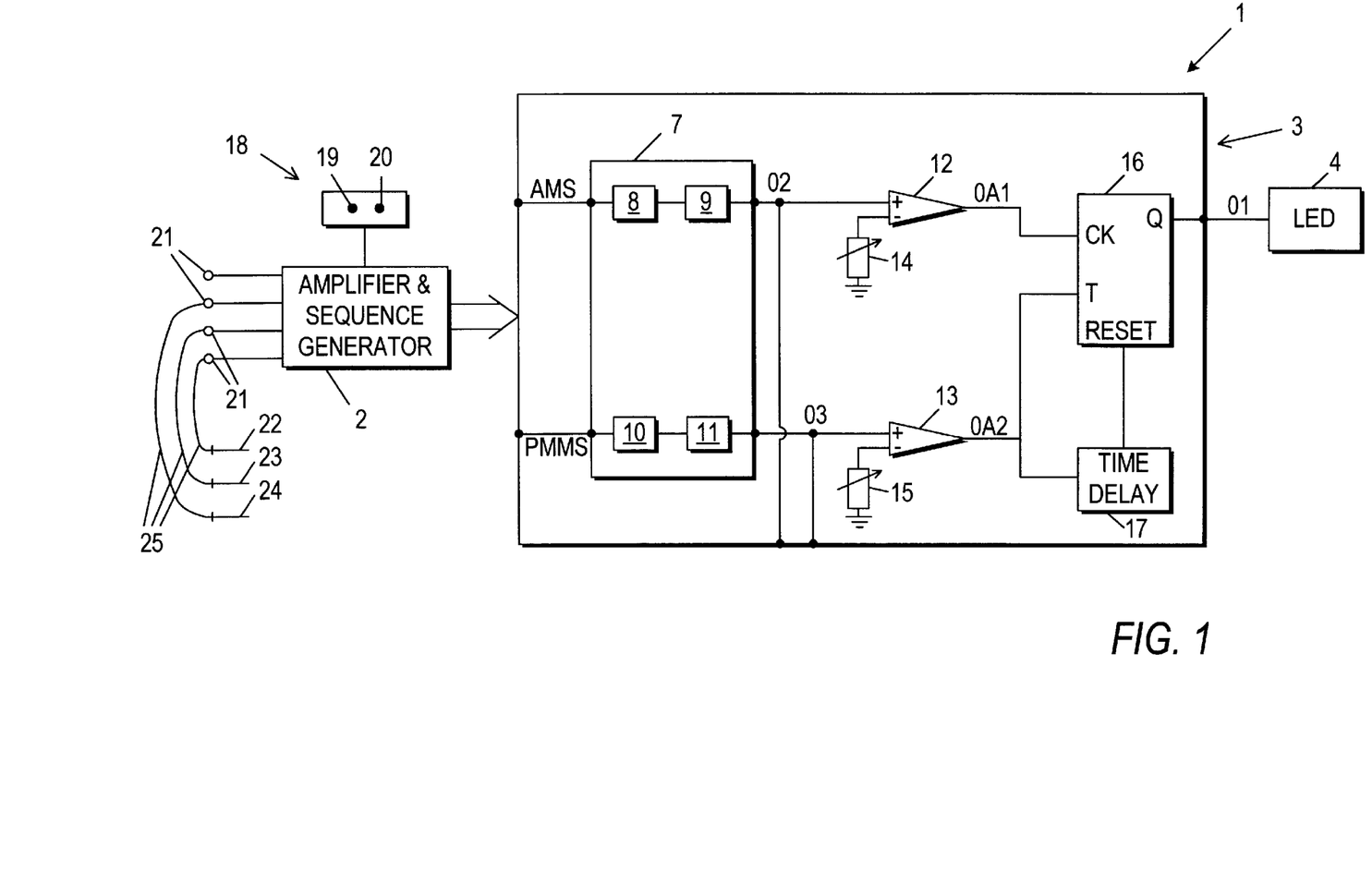
FIG. 1 is a first embodiment of a diagnostic apparatus according to the invention.

Referring to FIG. 1, there is illustrated a diagnostic apparatus 1 comprising amplifier and sequence generator circuitry 2 which can be, but not necessarily, a programmable EMG which is electrically connected to processing circuitry 3. A first output O1 of circuitry 3 is electrically connected to a light emitting diode 4. Apparatus 1 also includes a signal box 18 which houses two light emitting diodes 19, 20 electrically connected to EMG 2 which may be either bipolar or monopolar. There are a number of EMG inputs 21 for connection of electrodes 22, 23, 24 by leads 25 in which one or more electrodes 22 are adapted to be inserted into muscles of a patient. One or more electrodes 23 are surface electrodes adapted to be attached to a skin surface of the patient in close proximity to a prime mover muscle to be used in diagnosis of LBP. Further, electrode 24 is a ground electrode which is usually attached to a stable bony prominence such as the anterior superior iliac spine, lateral epicondyle of the femur or fibular head.

In an alternative form, both electrodes 22 and 23 may be adapted to be attached to the skin surface in close proximity to the muscles of interest to thereby generate electrical signals by acoustic myography.

Processing circuitry 3 includes a primary processing circuit 7 having a first rectifier 8 and associated filter 9 for rectifying and processing an anticipatory muscle signal (AMS) received from EMG 2. Circuit 7 also has a second rectifier 10 and associated filter 11 for rectifying and processing a prime mover muscle signal (PMMS) also received from EMG 2. Filters 9 and 11 are band pass filters having a bandwidth of 20 Hz to 1 kHz.

Circuit 7 has two outputs O2, O3 which are connected to a non-inverting input of a respective operational amplifier 12, 13. Outputs O2, O3 of circuitry 3 may also be electrically connected to an analogue to digital converter 5, the output of which is connected to a computer 6.

Inverting inputs of each operational amplifier 12, 13 are connected to one end of a respective variable resistor 14, 15 the other ends being connected to ground.

An output OA1 of operational amplifier 12 is connected to a clock input CK of a T-type flip-flop 16 in which the flip-flop is activatable upon a rising transition on OA1. An output OA2 of operational amplifier 13 is connected to an input T of flip-flop 16 and output Q is wired to output O1 which is connected to display 4. Output OA2 is also connected to an active low reset of flip-flop 16 via a time delay circuit 17.

When using a monopolar EMG 2, electrode 22 is inserted into an anticipatory muscle such as the transversus abdominis. Electrode 22 may be fine wire electrodes fabricated from 75 $\mu$m teflon-coated stainless steel wire as described by Basmajian and Stecko (1962, J. Appl. Phys., 17, 849). However, other types of electrodes such as concentric needle electrodes may be used.

If the anticipatory muscle used is the transversus abdominis, insertion is 2 cm anterior to the rib cage from a line projected vertically from the ASIS, abdominis obliquus externus, half way between the iliac crest and caudal border of the rib cage in the mid axillary line and abdominis obliquus internus, 3 cm medial and superior to the ASIS. Further, electrode 23 is placed on a skin surface in close proximity to the prime mover muscle associated with a limb to be moved.

When the patient is relaxed, apparatus 1 is used to diagnose LBP caused by muscular dysfunction which is best described with reference to the flow diagram of FIG. 2. Initially, variable resistors 14, 15 are adjusted to define a reference threshold value associated with respective inputs AMS and PMMS. Each reference value defines a voltage threshold value at which the respective operational amplifier outputs OA1, OA2 which switch from a low to high logic value (0 volts to 5 volts) or vice versa. Ideally, a voltage level of the threshold value of operational amplifier OA1 should be slightly higher than the voltage level of the threshold value of operational amplifier OA2.

Figure 2:
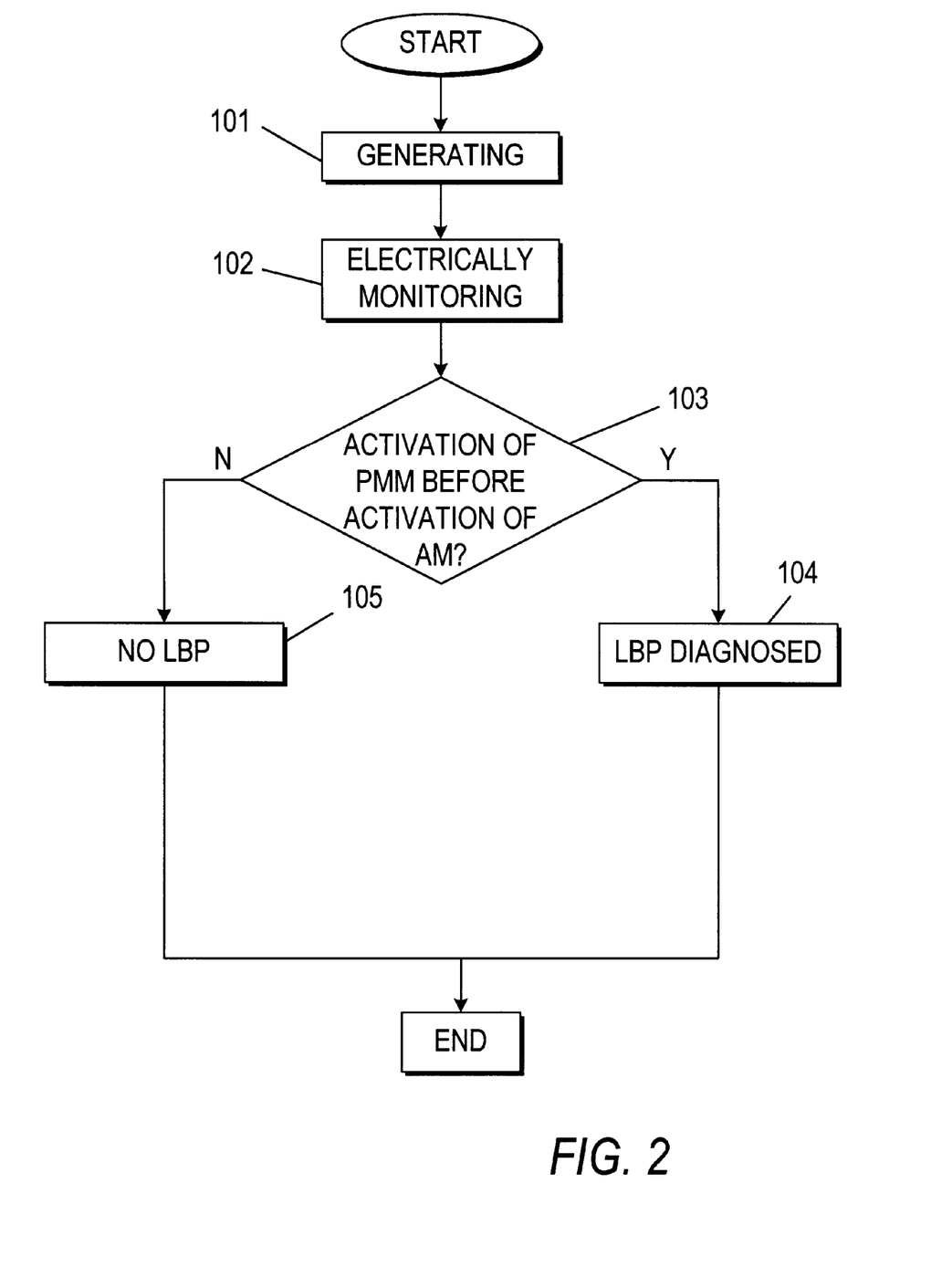
FIG. 2 is a flow diagram illustrating how the apparatus of FIG. 1 is used to diagnose LBP caused by muscular dysfunction.

As illustrated in FIG. 2, it is assumed that the patient is relaxed and waiting for instruction signal by EMG 2 and signalled by light emitting diodes 19, 20. In this embodiment, the step of generating 101 comprises sequentially the step of warning followed by the step of instructing. The step of warning is effected by activating LED 19 which provides a first signal that informs the person to prepare for voluntary movement of the limb associated with the prime mover muscle. The step of instructing is effected by activating LED 20 which provides a second signal to thereby instruct the patient to voluntarily move the limb.

Electrical signals generated from electrodes 22, 23 are amplified by EMG 2 and are continually monitored as illustrated at step 102 by circuit 3. At step 103 a time sequence of activation is determined. If the sequence of activation of the prime mover muscle occurs before activation of the anticipatory muscle, OA2 will switch from low to high before OA1 switches from low to high. Accordingly, output Q of flip-flop 16 will toggle from low to high as input T will be high prior to activation of clock input CK. Thus, LBP is diagnosed at step 104, by activation of light emitting diode 4. Alternatively, if the sequence of activation of the anticipatory muscle occurs before the activation of the prime mover muscle, signal OA1 will go from low to high before OA2. Accordingly, output Q of flip-flop 16 will remain at a logic 0 thus, absence of LBP is diagnosed at step 105 by light emitting diode 4 remaining in an "off" state.

As discussed above, the reference levels of operational amplifiers OA1, OA2 are adjusted so that the reference level of OA1 is higher than the reference level of OA2. This allows for a time delay to provide an adjustable confidence level associated with diagnosis of lower back pain. In such a diagnosis, it is assumed that if both OA1 and OA2 go high simultaneously, the absence of LBP is diagnosed.

Time delay 17 which is the order of four seconds resets flip-flop 16 thereby allowing for the above method to be repeated a number of times to validate the diagnosis. Furthermore, if analogue to digital converter 5 is connected to outputs O2, O3, then output signals of O2, O3 can be digitised and stored on computer 6. The digitised signals can then be analysed "off line" by suitable software as illustrated in Appendix I.

Figure 3:
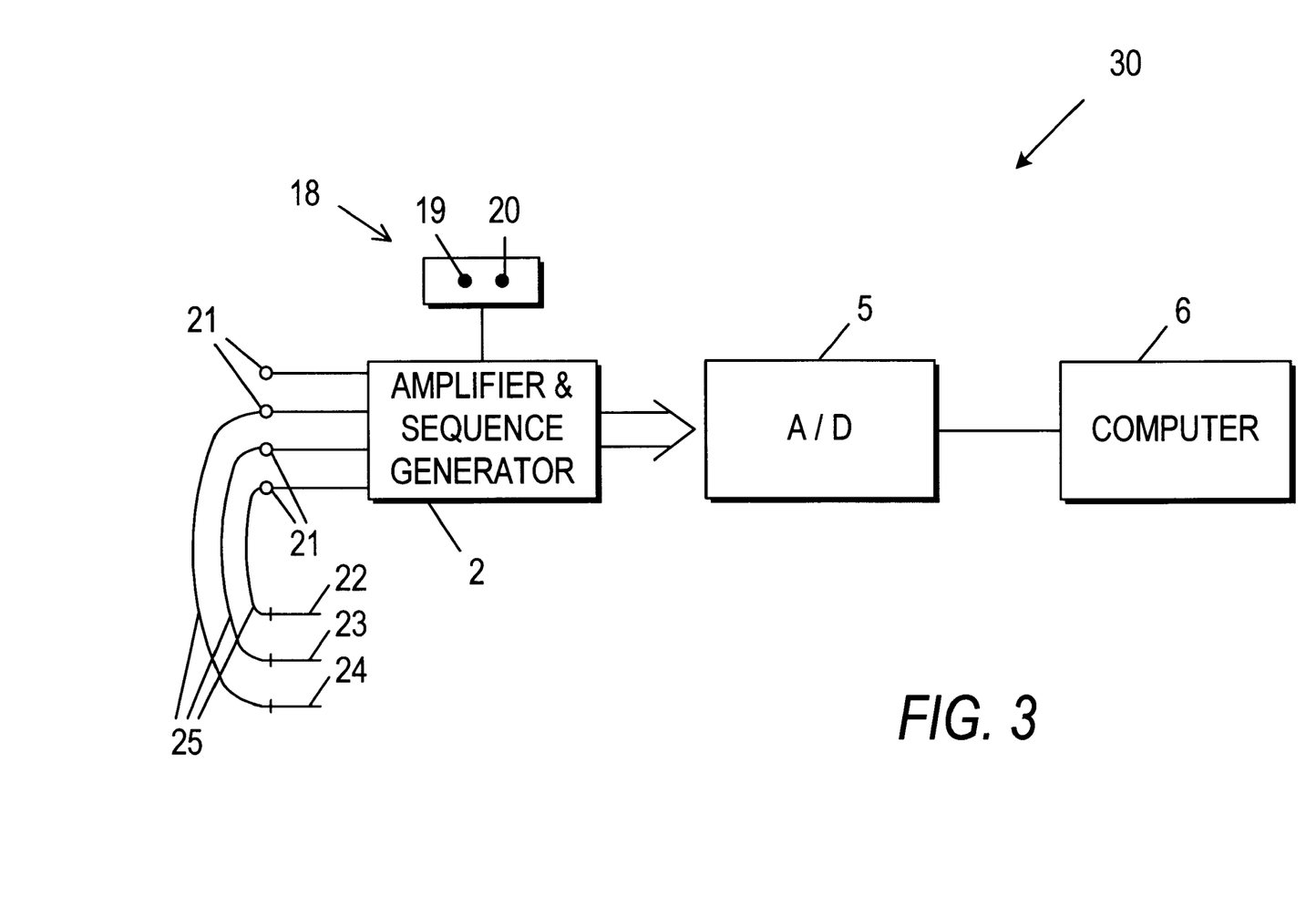
FIG. 3 is a second embodiment of a diagnostic apparatus according to the invention.
Figure 4A:
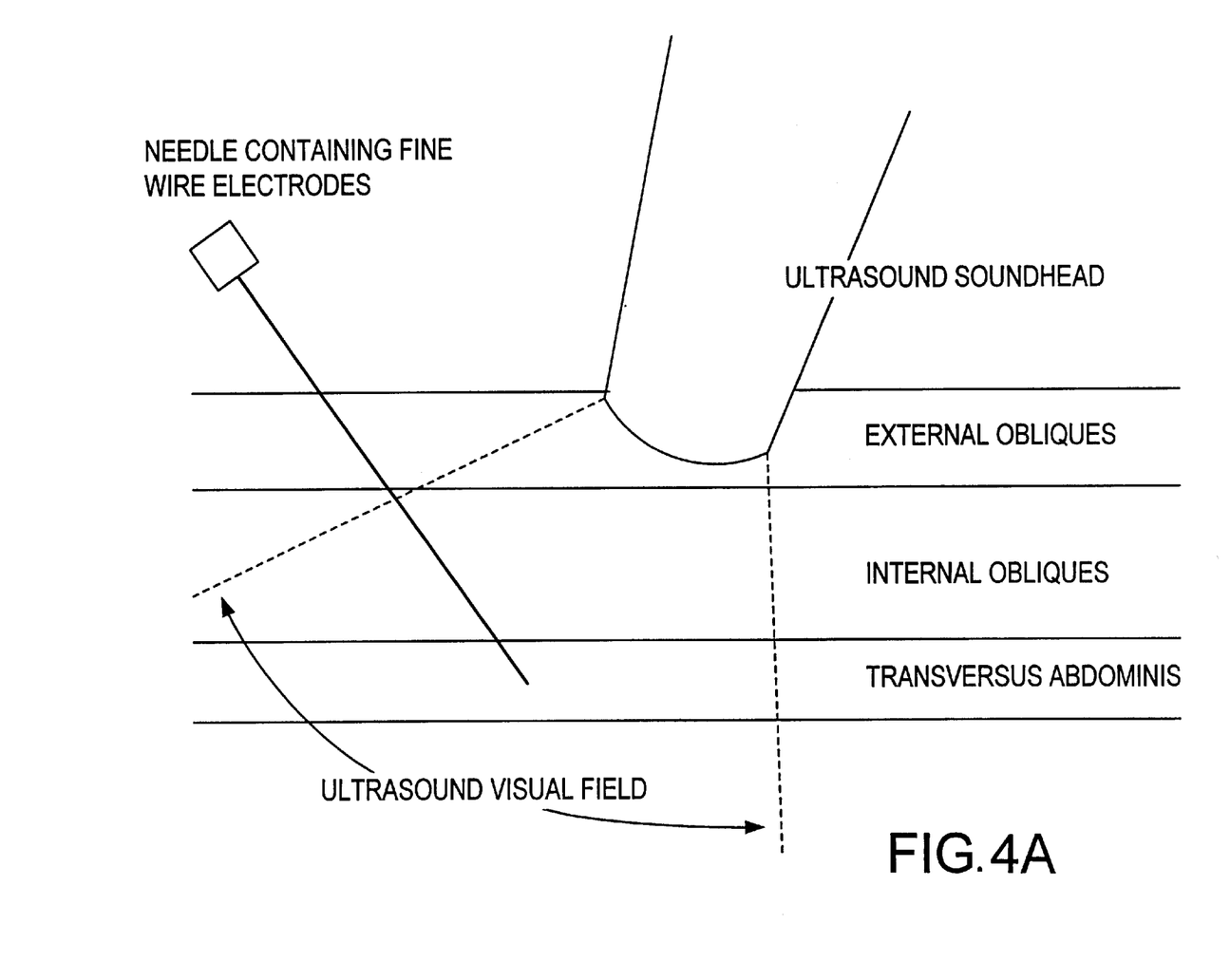
FIG. 4A is an illustration of an ultrasound scan of an abdominal wall needle placed into the transversus abdominis.
Figure 4B:
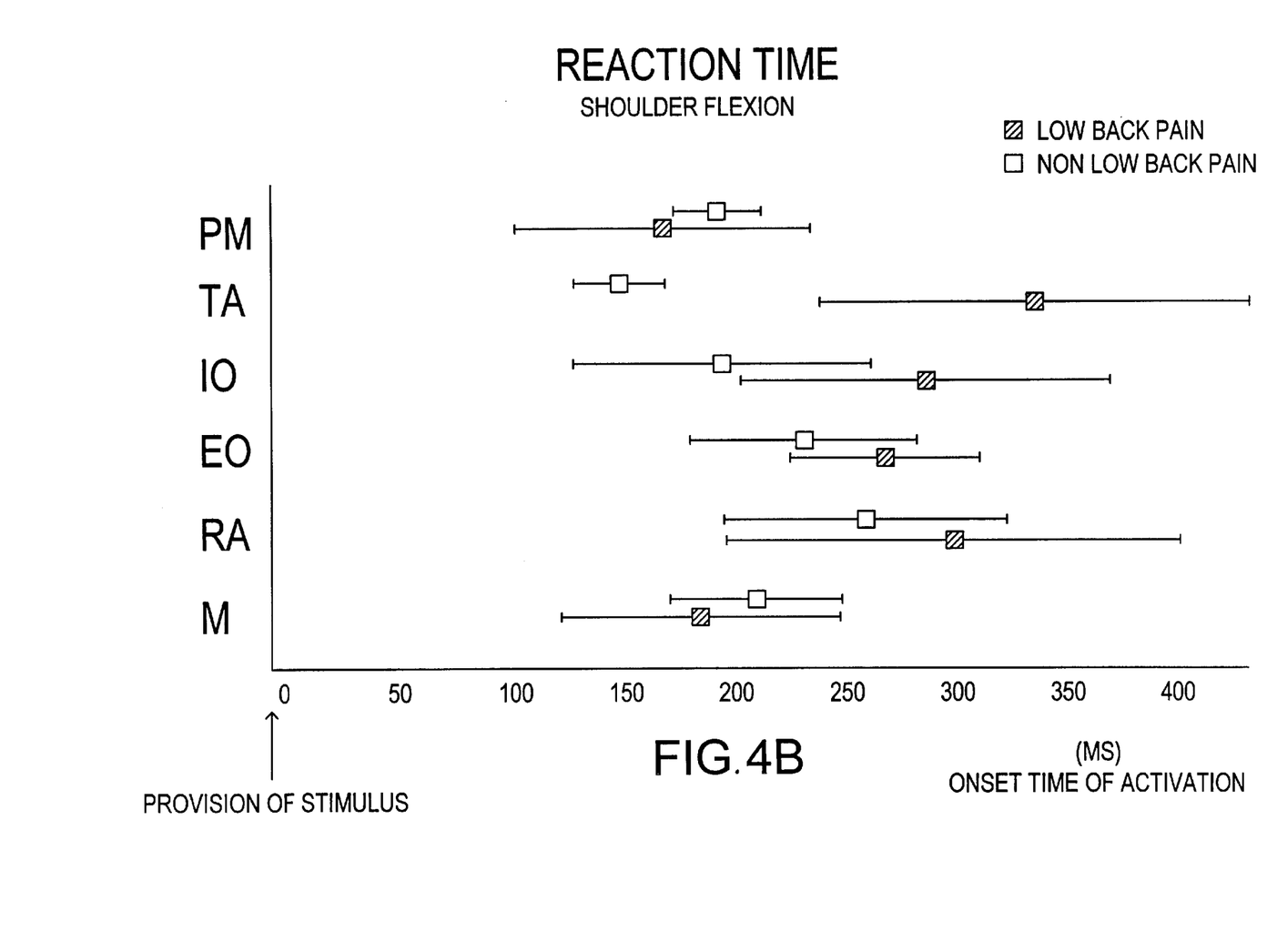
FIG. 4B is a graphical representation of reaction times from onset of visual stimulus on onset of increase in EMG activity for all muscles averaged over all upper limb movements.

In FIG. 3, a second embodiment of a diagnostic apparatus 30 is illustrated. Apparatus 30 is similar to apparatus 1, the difference being that processing circuitry 3 and light emitting diode 4 are replaced with analogue to digital converter 5 and computer 6.

In use, the AMS and PMMS are digitised by analogue to digital converter 5 and then stored on computer 6. A number of diagnostic trials may then be conducted upon the patient after which computer 6 processes the digitised data to diagnose if the patient has LBP caused by muscular dysfunction as discussed above with reference to FIG. 2. The diagnosis is dependent upon the time sequence of the AMS relative to the PMMS. An example program for processing the digitised data is shown in Appendix I.

The program averages the magnitude of the digitised signals over a period of time to provide an average magnitude value associated with the AMS and PMMS. This is achieved by rectifying and band pass filtering, between 20 Hz and 1 kHz, of the digitised signals after which the signals are averaged over a period of time.

A root mean square value of the average magnitude value of each of AMS and PMMS is calculated to provide the anticipatory muscle reference value and prime mover muscle reference value respectively.

The threshold value associated with the AMS is at least two standard deviations greater than the anticipatory muscle reference value. Similarly, the threshold value associated with the PMMS is at least two standard deviations greater than the prime mover muscle reference value.

The processing of the digitised data may also include detecting when at least one of the monitored signal magnitudes increases above the determined threshold value thereof before an expiration of a time frame associated with the instruction signal(s). If this condition occurs, an invalidating signal indicative of this sequence being invalid is provided and, if required, further analysis of the digitised data is conducted.

Further, if required, a time delay may be provided between the start of each of the warning and instructing signals which time delay may vary randomly. Variation of the time delay is preferable because the patient is unable to anticipate the time at which the signals are given. As a consequence, this may decrease the probability of the patient voluntarily moving the limb prior to the instructing step.

Although the invention is with reference to preferred embodiments, it is to be understood that the invention is not limited to the specific embodiments described herein.

EXPERIMENTAL

To further aid in understanding the invention, the results of experiments performed with the preferred embodiment are presented with reference to diagrams in which:

FIG. A refers to an illustration of an ultrasound scan of abdominal wall needle placed into transversus abdominis; and FIG. B refers to a graphical representation of reaction times from onset of visual stimulus to onset of increase in EMG activity for all muscles averaged over all upper limb movements.

Subjects

Nine male and six female subjects (20.6±2.3 years) of average height (174±9 cm) and weight (69±1.1 kg) participated in the study. Subjects were normally active and were excluded if they had any history of LBP, lower limb pathology, gross postural abnormalities or involvement in high intensity training.

Electromyographic Recordings

Bipolar fine-wire electrodes were used for the collection of EMG data from the transversus abdominis (TA), abdominis obliquus internus (IO) and abdominis obliquus externus (EO). These electrodes were fabricated from 75 $\mu$m teflon coated stainless steel wire (A-M Systems Inc., USA) in the manner described by Basmajian and Stecko (1962, J. Appl. Phys., 17, 849). Due to the narrow width of TA, particular care had to be taken to ensure that the bend ends and exposed areas were sufficiently small to prevent inaccurate recordings from the adjacent IO.

To ensure accurate placement of the electrodes, insertion was performed under the guidance of real-time ultrasound imaging (RTUI) using a 5 MHz curved array sound head (FIG. A). RTUI allows clear visualisation of the muscles, fascia and underlying structures as well as the needle providing a means to position accurately the electrode within the muscle belly (Cresswell et al., 1992, Acta Physiol. Scand., 144, 409–418; DeTroyer et al., 1990, J. Appl. Phys., 68, 1010–1016). Application of externally applied anaesthetic EMLA cream (Astra Pharmaceuticals, Australia) preceded the needle insertion to minimise cutaneous sensation of needle insertion.

The electrodes were positioned at sites similar to those suggested by Cresswell et al., (1992, Acta Physiol. Scand., 144, 409–418). The only variation was that these electrodes were on stable bony landmarks rather than the umbilicus. The TA electrode was placed 2 cm anterior to the rib cage from a line projected vertically from the ASIS, EO, half way between the iliac crest and caudal border of the rib cage in the mid axillary line and IO, 3 cm medial and superior to the ASIS. Following insertion, the needle was removed with care to leave the wires in an appropriate position.

Surface electrodes were placed over rectus abdominis (RA) and multifidus (M) parallel to the muscle fibres with an interelectrode spacing of 12 mm. Consistent electrode sites were used, RA mid way between the umbilicus and pubic symphysis close to the midline in a cephalo-lateral direction and multifidus, 2 cm adjacent to the spinous process at the L4-5 level. Surface electrodes were similarly placed over the muscle belly of the prime mover for each movement: shoulder flexion—anterior deltoid; shoulder abduction—middle deltoid; shoulder extension—posterior deltoid.

Procedure

In the standing position, maintaining normal compression and proprioceptive information from the lumbar segments, ten repetitions of unilateral flexion, abduction and extension of the shoulder were performed in random order. Adequate rest periods were allowed between each movement during which the subject adopted the sitting position. Prior to movement, the subjects were requested to reduce consciously the background level of activity of the abdominals, directed by verbal feedback from the examiner who monitored the activity on the computer screen. The subject maintained equal weight bearing with auditory feedback of accuracy provided by a Balance Performance Monitor (SMS Healthcare, UK).

Movement stimulus was provided visually by two light emitting diodes (LED) on a display board placed 1.5 m from the subject at eye level. The stimuli were provided in the standard manner used for reaction time tasks involving a warning stimulus preceding the movement stimulus by a random period between 0.5–4 sec. Each subject was requested to remain relaxed when given the warning stimulus and not respond until given the stimulus to move. Movement was performed as fast as possible with emphasis on accuracy of speed and not accuracy of distance. Five practice repetitions were allowed prior to EMG recording. Shoulder flexion and abduction were performed to approximately 60° and shoulder extension to approximately 40°.

The entire procedure was repeated on 5 subjects several weeks after the initial testing session. The pattern of activation recorded for each muscle was repeatable between testing sessions, although, variation was recorded between the actual data.

Data Management

Frequent base line EMG activity, although reduced by conscious relaxation, made visual determination of the onset of muscle activity inappropriate. To increase the objectivity of the measurement of onset, an algorithm was developed that selected the point where the mean of 50 consecutive samples (25 ms) was greater than 2 standard deviations from the mean baseline activity recorded for 50 ms prior to the warning stimulus. Prior to evaluation, the data was rectified and smoothed using a 50 Hz seventh order low pass elliptic filter. Prior to implementation of the algorithm, the validity of the method was checked against visual determination of onset time, the described method was found to correlate highly with visually determined onset times ($p<0.0001$). Each onset time was checked visually to ensure that the timing was valid and meaningful. Trials were rejected if heart activity or movement artefact made the onset time impossible to determine. In a small number of trials where the computer derived onset time was invalid for any reason, the onset was visually determined if there was a clearly defined onset point. For each muscle the pre-motor reaction time (RT) and onset time relative to the onset time of the prime mover (the muscle-prime mover difference time (DT)) were evaluated.

Due to the slow action potential conduction along muscle fibres (3–5 m/s), the determine of onset time from fine-wire EMG is subject to error. The depth and proximity of TA and the oblique abdominals precludes the use of electrical stimulation for the location of the motor point. However, because the prime mover muscle activity was consistently recorded using surface electrodes, which results in only a small delay due to the propagation time through the subcutaneous tissues, the results can only underestimate the degree of anticipation of the abdominal muscles. For this reason the percentage of trials in which the DT was negative (indicating anticipatory activation) irrespective of the magnitude of this period was an additional parameter evaluated.

The analysis was based on the mean over the 10 repetitions for each movement and subject. The RT, DT and the percentage of anticipatory trials were evaluated within and between movements using analysis of variance (ANOVA) statistics. Post-hoc Duncan's multiple range tests were used to further evaluate the significant differences. The percentage of anticipatory trials was arcsin transformed prior to ANOVA analysis to improve the accuracy of the analysis.

Generalised Pattern of Activation

Prior to conscious relaxation, activity of TA was recorded at rest in all subjects in the standing position. Relative reduction of this activity prior to movement was achieved in all subjects. Activation of each of the abdominal muscles and the L4-5 multifidus occurred with all movements, although the pattern of muscle activation varied between movements. In all movements, the activation of TA preceded the activation of the prime mover (Table 1) and when more than one trunk muscle was active in anticipation, TA was consistently the first muscle active. The frequency with which the other lumbar muscles exhibited anticipatory activation was dependent on direction of movement.

To assess if any change in RT occurred over the 10 repetitions performed for each movement, linear regressions of repetitions by movement for each subject were calculated. Of the resultant 900 analyses only a very small number exhibited significant linear regression by repetition.

Upper Limb Movement Grouped Across Directions

The mean RT for upper limb movement measured from the presentation of visual stimulus to onset of EMG (pre-motor reaction time) for the prime mover for each movement direction was 165±40 ms. Irrespective of direction of movement, TA was the first muscle active with a mean RT of 136±32 ms preceding the onset of prime mover activation by 29±35 ms (p<0.0001). Although the onset of IO activity preceded that of the prime mover by 5±53 ms, this difference was not significant. The onset of RA, EO and M activity followed the activation of the prime mover by 25±64 ms, 33±65 ms and 57±74 ms, respectively. Only the latencies of EO and M differed significantly from the prime mover (p<0.0001). The larger variations noted for the recordings may be explained by the error, hereinabove discussed, associated with relative innervation zone and electrode placement.

Shoulder Flexion

With forward movement of the upper limb, the onset of TA preceded that of all other muscles, significantly earlier than the other truck muscles (p<0.0001) (Table 1). Although the grouped data revealed a significant distinction between the activation of TA and PM, when movements were analysed individually, the trend for earlier activation of TA (32±37 ms) was not significant and is considered to be due to the high intersubject variation. The onset of IO, M, RA, EO followed the activation of PM in order of increasing length of RT. Only the difference between IO and EO was significant (p<0.0001). TA was active in anticipation of PM in 80±19% of 150 repetitions (15 subjects, 10 repetitions) which is significantly greater than the other lumbar muscles (p<0.0001) (Table 2). Although the mean onset of activity for the other trunk muscles occurred after the PM, over all repetitions, up to 53±34% (IO) of the trials resulted in anticipatory activation. This indicates that during the performance, controlled limb movement variation exists in the pattern of muscle activation across repetitions and between subjects.

Shoulder Abduction

Coincident upon shoulder abduction, the onset of TA and IO preceded that of PM (Table 1) and did not differ significantly from each other. The onset of activation of EO, RA and M followed that of the prime mover with increasing magnitude of RT, without significant difference between the onset times. The difference between IO and EO failed to reach statistical significance. The number of anticipatory trials was significantly greater for TA than the other trunk muscles (p<0.0001) (Table 2).

Shoulder Extension

The RT for TA, RA and IO preceded PM with no significant difference between the muscles, EO and M followed the activation of the PM and were not significantly different from the RT or IO. The lowest percentage of anticipatory TA trials (67±26%) and the greatest number of anticipatory RA trials (58±26%) accompanied shoulder extension (Table 2).

Comparison Between Movements

There was no significant difference in the RT of PM, TA and IO between movements coincident upon upper limb movement. Statistically significant direction-specific differences were recorded for the RT of EO, RA and M and due to the consistent RT for PM, resulted in variation of the relationship between the activation of these muscles and PM. RA, a primary trunk flexor, was activated earliest in shoulder extension (p<0.004). The laterally placed EO, with actions in both trunk flexion and lateral flexion, had significantly shorter onset latencies in respect of shoulder extension and abduction compared to flexion (p<0.004). The RT for M, a trunk extensor and rotator, was shortest for shoulder flexion and abduction (p<0.001).

The percentage of trials resulting in anticipatory activation of the trunk muscles was consistent with these data. With upper limb movement, RA was more commonly anticipatory with shoulder extension (p<0.0001), EO with abduction and extension (p<0.0001) and multifidus with flexion (p<0.0001).

Conversely, the RT for TA and IO exhibited non-direction specificity and was consistent between movements although there was a non-significant trend for a more latent activation of IO with shoulder flexion. No significant variation exists between the number of anticipatory trials for TA and IO between movements.

In a preliminary study of 16 subject, including 8 chronic back pain subjects and 8 age and sex-matched control subjects, the RT of abdominal muscles relative to activation of the anterior deltoid (PM) were evaluated. The results of this study, summarised in FIG. B, show that, unlike other abdominal muscles tested, there is little if any overlap between the range of the onset time of activation of TA relative to that of PM for both the control subjects and the back pain subjects. Accordingly, it is suggested that TA is the most suitable anticipatory muscle for diagnosis of LBP.

TABLE 1

Muscle Reaction Times (RT) and Difference Times (DT) (ms ± SD)

|    |    | Shoulder Flexion | Shoulder Abduction | Shoulder Extension |
|----|----|------------------|--------------------|--------------------|
| PM | RT | 166 ± 35         | 170 ± 53           | 160 ± 31           |
| TA | RT | 134 ± 19         | 134 ± 39           | 142 ± 36           |
|    | DT | −32 ± 37         | −36 ± 40           | −19 ± 27           |
| IO | RT | 181 ± 59         | 152 ± 55           | 156 ± 51           |
|    | DT | 14 ± 58          | −25 ± 56           | −3 ± 38            |
| EO | RT | 227 ± 58         | 178 ± 48           | 188 ± 68           |
|    | DT | 60 ± 56          | 8 ± 74             | 30 ± 56            |
| RA | RT | 222 ± 60         | 200 ± 73           | 147 ± 35           |
|    | DT | 57 ± 54          | 29 ± 84            | −9 ± 24            |
| M  | RT | 183 ± 39         | 213 ± 68           | 258 ± 94           |
|    | DT | 18 ± 39          | 54 ± 70            | 98 ± 90            |

TABLE 2

Percentage of anticipatory trials (negative difference time)
(% ± SD)

|  | TA | IO | EO | RA | M |
|---|---|---|---|---|---|
| Shoulder Flexion | 80 (±19) | 53 (±34) | 24 (±18) | 30 (±25) | 43 (±27) |
| Shoulder Abduction | 73 (±19) | 48 (±25) | 43 (±20) | 31 (±24) | 24 (±21) |
| Shoulder Extension | 67 (±26) | 49 (±32) | 31 (±26) | 58 (±26) | 22 (±24) |

APPENDIX I

```
function [onset.rms] = on_calf(num_trials,warn_time,
            start_time,data,f,sf);
%   routine to calculate onset of EMG
%   rectify
%   low-pass filter (f Hz);
%   calculate baseline mean & standard deviation
%   transverse from start time for 2 secs to see if there is an onset
%      onset is defined as the point where 25 ms of rectified data is >
%      mean + 2 SD of base line
%   calculate low-pass filter co-eff at f Hz
%   w = f/(sf/2);
%   [b,a] = ellip(6, 0.1, 20, w);
load filtcoef
if (sum(isnan(data)) ==0)
%   substract mean and rectify
      z = abs(data -mean(data));
y = filtfilt(b,a,z);
for i=1:num_trials
%   calculate baseline SD
      x = y(warn_time(i):warn_time(i)+99);
      Mbline(i) = mean(x);
      Sbline(i) = sqrt(1/(length(x)-1)*sum ((x-Mbline(i)).^ 2));
%   calculate onset. If SD > 2* bline for 25 samples then got it
%   start at start time (+100 ms because any reaction faster than this
                is invalid)
      for 2 secs. I
%   found than say onset time = -1
      stop = 0;
      n = start_time(i)+200;
      n4000 = min(n+4000,length(y));
      while ((n < n4000) & (stop ==0))
      if(sum(y(n:min(length(y),n+50)) > (Mbline(i) + 2*Sbline(i))) >49)
      stop =1;
      end
      n=n+1;
      end
      if (stop ==0) onset (i) = -1;
      else onset (i) = n;
      end
%   Calculate:
%   - calculate EMG baseline statistics prior to this (50 msecs),
                call this bsd
%   - calculate the 'running' statistics from t1, call this sd
%   - if the sd is > 2* bsd for M number of samples then voila got it.
%   read or load signal timing
      warn_time = _% value of first signal
      start_time = _% value of second signal.
%   calculate EMG onset of muscle 1
      eval(['load' onea]);
      [onsetla,rmsla] = on_calf(warn_time, start_time,data,50,2000);
          %includes
      filter data (50 and
%   calculate EMT onset of muscle 2
      eval (('load' oneb]);
      [onsetlb,rmslb] = on_calf(warn_time, start_time,data,50,2000);
      eval (['save' onea '@']); % saves the results as a new file
```

We claim:

1. A diagnostic apparatus for diagnosis of LBP caused by neuromuscular dysfunction, said apparatus comprising:
a monitoring means for monitoring an anticipatory muscle signal resulting from one or more electrodes associated with an anticipatory muscle and a prime mover muscle signal resulting from one or more electrodes associated with at least one prime mover muscle associated with a limb; and
a processing means for detecting a variation in the time of onset of the anticipatory muscle signal relative to the time of onset of the prime mover muscle signal for providing diagnosis of presence or absence of LBP.

2. The diagnostic apparatus of claim 1 wherein LBP is diagnosed when activation of the prime mover muscle occurs before activation of the anticipatory muscle.

3. The diagnostic apparatus of claim 1 wherein absence of LBP is diagnosed when activation of the anticipatory muscle occurs prior to or concurrently with activation of the prime mover muscle.

4. The diagnostic apparatus of claim 1 further comprising a signal generator means for generating one or more instruction signals.

5. The diagnostic apparatus of claim 4 wherein the signal generator means provides two sequential instructions.

6. The diagnostic apparatus of claim 4 wherein the signal generator means provides a time delay between the start of each of the instruction signals.

7. The diagnostic apparatus of claim 4 wherein the signal generator means provides a randomly variable time delay between the start of each of the instruction signals.

8. The diagnostic apparatus of claim 1 wherein the processing means provides an output signal indicative of the presence or absence of LBP when the prime mover muscle signal and the anticipatory muscle signal increase above a threshold value.

9. The diagnostic apparatus of claim 8 wherein there is a different threshold value associated with each of the prime mover muscle signal and the anticipatory muscle signal.

10. The diagnostic apparatus of claim 9 wherein the different threshold value associated with each of the prime mover muscle signal and the anticipatory muscle signal are manually adjustable.

11. The diagnostic apparatus of claim 9 wherein the processing means is adapted to calculate each of the said different threshold values.

12. The diagnostic apparatus of claim 1 further comprising a signal conversion means to convert both the prime mover muscle signal and anticipatory muscle signal into corresponding digitised signals.

13. The diagnostic apparatus of claim 12 further comprising a digital storage means for storing the digitised signals.

14. The diagnostic apparatus of claim 13 wherein the processing means is a computer or programmable processor.

15. The diagnostic apparatus of claim 14 wherein the digital storage means is part of the computer or programmable processor.

16. The diagnostic apparatus of claim 12 wherein the apparatus is adapted to average the digitised signals over a period of time to provide signal reference values.

17. The diagnostic apparatus of claim 16 wherein the processing means provides an output signal indicative of the presence or absence of LBP when the prime mover muscle signal and the anticipatory muscle signal increase above the corresponding signal reference values thereof.

18. A method for diagnosis of LBP caused by neuromuscular dysfunction, said method including the steps of:
(i) initiating a voluntary movement of a limb;
(ii) electrically monitoring activation of at least one anticipatory muscle relative to activation of at least one prime mover muscle associated with the limb; and
(iii) comparing time of onset of activation of the at least one anticipatory muscle relative to time of onset of activation of the at least one prime mover muscle to diagnose presence or absence of LBP.

19. The method of claim 18 wherein presence of LBP is diagnosed when the time of onset of activation of the prime mover muscle occurs before the time of onset of activation of the anticipatory muscle.

20. The method of claim 18 wherein the absence of LBP is diagnosed when the time of onset of activation of the anticipatory muscle occurs prior to or concurrent with the time of onset of activation of the prime mover muscle.

21. The method of claim 18 further including the step of generating one or more instruction signals to instruct voluntary movement of the limb.

22. The method of claim 21 wherein a first and a second instruction signals are generated sequentially such that the first instruction signal functions as a warning signal which informs the patient to prepare for voluntary movement of the limb associated with the prime mover muscle and the second instruction signal instructs voluntary movement of the limb.

23. The method of claim 21 wherein a time frame between each of the one or more instruction signals is varied randomly.

24. The method of claim 18 further including the step of determining when an electrical signal associated with activation of the prime mover muscle and an electrical signal associated with activation of the anticipatory muscle increase above a threshold value.

25. The method of claim 23 wherein there is a different threshold value associated with the activation of each of the electrical signals.

26. The method of claim 23 further including the step of determining a muscle signal reference value associated with respective anticipatory and prime mover muscles when relaxed by averaging signals from respective muscles over multiple measurements.

27. The method of claim 23 further including the step of averaging the electrical signals over a period of time to provide an average magnitude value.

28. The method of claim 26 further including the step of comparing each of the electrical signals when the average magnitude value of each of the electrical signals increases above a respective threshold value to provide a time sequence wherein the threshold value of the anticipatory muscle signal is related to the anticipatory muscle signal reference value and the threshold value of the prime mover muscle signal value is related to the prime mover muscle signal reference value.

29. The method of claim 26 wherein diagnosis of the presence of LBP occurs if the average magnitude value of the prime mover muscle signal increases above the threshold value thereof prior to when the average magnitude value of the anticipatory muscle signal increases above the threshold value thereof.

30. The method of claim 26 wherein absence of LBP is diagnosed if the average magnitude value of the anticipatory muscle signal increases above the threshold value thereof prior to or concurrent with when the average magnitude value of the prime mover muscle signal increases above the threshold value thereof.

31. The method of claim 18 further including the step of analysing multiple measurements to validate the diagnosis.

32. The method of claim 18 wherein the anticipatory muscle is selected from the group including transversus abdominis and multifidus.

33. The method of claim 18 wherein the prime mover muscle is selected from the group including anterior deltoid, middle deltoid and posterior deltoid.

34. The method of claim 18 wherein the prime mover muscle is associated with the upper limbs or arms of a patient.

35. The method of claim 18 wherein the prime mover muscle is associated with the lower limbs or legs of a patient.

36. The method of claim 34 wherein the anticipatory muscle is selected from the group including transversus abdominus, internal oblique, external oblique, rectus abdominis and multifidus.

37. The method of claim 34 wherein the prime mover muscle is selected from the group including rectus femoris, tensor fascialatae, biceps femoris, gluteus maximus, semi-membranosis or semi-tendonosis.

38. The method of claim 34 wherein the initial voluntary movement of the limb refers to flexion, abduction or extension of the limb.

* * * * *